US012778394B2

(12) United States Patent
Petrova et al.

(10) Patent No.: US 12,778,394 B2
(45) Date of Patent: Nov. 3, 2026

(54) END EXPANDABLE OPTICAL FIBER BUNDLE

(71) Applicants: Baylor College of Medicine, Houston, TX (US); William Marsh Rice University, Houston, TX (US)

(72) Inventors: Elena Petrova, Houston, TX (US); Sharmila Anandasabapathy, Houston, TX (US); Rebecca Richards-Kortum, Bellaire, TX (US)

(73) Assignees: Baylor College of Medicine, Houston, TX (US); William Marsh Rice University, Houston, TX (US)

( * ) Notice: Subject to any disclaimer, the term of this patent is extended or adjusted under 35 U.S.C. 154(b) by 458 days.

(21) Appl. No.: 18/041,823

(22) PCT Filed: Aug. 25, 2021

(86) PCT No.: PCT/US2021/071271

§ 371 (c)(1),
(2) Date: Feb. 16, 2023

(87) PCT Pub. No.: WO2022/051741

PCT Pub. Date: Mar. 10, 2022

(65) Prior Publication Data

US 2024/0023791 A1 Jan. 25, 2024

Related U.S. Application Data

(60) Provisional application No. 63/070,364, filed on Aug. 26, 2020.

(51) Int. Cl.

| | |
|---|---|
| ***A61B 1/00*** | (2006.01) |
| ***A61B 1/018*** | (2006.01) |
| ***A61B 1/04*** | (2006.01) |

(52) U.S. Cl.
CPC .... *A61B 1/00167* (2013.01); *A61B 1/000096* (2022.02); *A61B 1/018* (2013.01); *A61B 1/043* (2013.01)

(58) Field of Classification Search
CPC .......... A61B 1/00167; A61B 1/000096; A61B 1/018; A61B 1/043; A61B 1/063; A61B 1/07
See application file for complete search history.

(56) References Cited

U.S. PATENT DOCUMENTS 5,290,275 A * 3/1994 Kittrell ................ B23K 26/067 606/15
5,554,100 A * 9/1996 Leiner ...................... A61B 1/07 600/920

(Continued)

FOREIGN PATENT DOCUMENTS

WO 2020112500 A1 6/2020

OTHER PUBLICATIONS

International Search Report and Written Opinion, International Patent Application No. PCT/US2021/071271, May 13, 2022.

(Continued)

*Primary Examiner* — Anhtuan T Nguyen
*Assistant Examiner* — Shankar Raj Ghimire
(74) *Attorney, Agent, or Firm* — Saul Ewing LLP; Kathryn Doyle; Sean P. Ritchie

(57) ABSTRACT

Systems and corresponding methods for an end-expandable optical fiber bundle are described herein. In one aspect, an endoscope can include a plurality of optical fibers each having a proximal end and a distal end; at least one camera coupled to the proximal ends of the plurality of optical fibers; and a sleeve enveloping the plurality of optical fibers proximate to the distal ends and repositionable along the length of the plurality of optical fibers, such that the sleeve (Continued)

is configured to control an angle of bend for each of the plurality of optical fibers as the optical fibers advance past the sleeve.

18 Claims, 4 Drawing Sheets

(56) References Cited

U.S. PATENT DOCUMENTS

| | | | | |
|---|---|---|---|---|
| 6,572,608 | B1 * | 6/2003 | Lee | A61F 9/008 606/4 |
| 6,735,367 | B2 * | 5/2004 | Sanso | G02B 23/26 385/115 |
| 7,883,459 | B2 * | 2/2011 | Miyagi | A61B 1/0623 600/172 |
| 10,849,482 | B2 * | 12/2020 | Fukazawa | A61B 1/0669 |
| 2001/0029316 | A1 * | 10/2001 | Webb | G01N 21/6486 600/101 |
| 2003/0123825 | A1 * | 7/2003 | Sanso | G02B 23/2469 385/119 |
| 2003/0191368 | A1 | 10/2003 | Wang et al. | |
| 2007/0055106 | A1 * | 3/2007 | Moriyama | G02B 23/2423 600/172 |
| 2007/0118013 | A1 * | 5/2007 | Miyagi | A61B 1/07 600/176 |
| 2008/0008430 | A1 | 1/2008 | Kewitsch | |
| 2008/0132990 | A1 * | 6/2008 | Richardson | A61B 1/0607 623/1.11 |
| 2013/0066215 | A1 | 3/2013 | Tearney et al. | |
| 2015/0335248 | A1 | 11/2015 | Huang et al. | |
| 2017/0127927 | A1 * | 5/2017 | Lei | A61B 1/0011 |
| 2017/0231475 | A1 | 8/2017 | Mcweeney et al. | |
| 2018/0341101 | A1 * | 11/2018 | Heni | A61B 1/00193 |
| 2022/0346633 | A1 * | 11/2022 | O'Brien | A61B 1/00096 |

OTHER PUBLICATIONS

Hughes, M. , et al., "Fiber bundle endocytoscopy", Biomedical Optics Express, vol. 4, No. 12, Nov. 11, 2013, 2781-2794.

* cited by examiner

END EXPANDABLE OPTICAL FIBER BUNDLE

CROSS-REFERENCE TO RELATED APPLICATIONS

This application is a national phase application under 35 U.S.C. 371 of International Application No. PCT/US2021/071271, filed Aug. 25, 2021, which claims the benefit of priority of U.S. Provisional Patent Application Ser. No. 63/070,364, filed Aug. 26, 2020. The entire contents of each application is hereby incorporated by reference herein.

STATEMENT REGARDING FEDERALLY SPONSORED RESEARCH OR DEVELOPMENT

This invention was made with government support under Contract No. CA232890 "The Effectiveness of High Resolution Microendoscopy (HRME) in High Grade" awarded by the National Institutes of Health (NIH). The government has certain rights in the invention.

BACKGROUND OF THE INVENTION

Endoscopic screening in some cases can be challenging, for example, due to large surface areas, contoured surface areas, and the like, that require screening within a limited amount of time.

SUMMARY

Systems and corresponding methods for an end-expandable optical fiber bundle are described herein. In one aspect, an endoscope can include a plurality of optical fibers each having a proximal end and a distal end; at least one camera coupled to the proximal ends of the plurality of optical fibers; and a sleeve enveloping the plurality of optical fibers proximate to the distal ends and repositionable along the length of the plurality of optical fibers, such that the sleeve is configured to control an angle of bend for each of the plurality of optical fibers as the optical fibers advance past the sleeve.

This aspect can include a variety of embodiments. In one embodiment, the plurality of optical fibers are uncoupled to one another.

In one embodiment, the distal ends of the plurality of fiber optics define an aggregate circumference perpendicular to the length of the plurality of fiber optics, where the aggregate circumference is variable based on the position of the sleeve with respect to the distal ends and the angle of bend for each of the plurality of optical fibers. In some cases, a minimum size for the aggregate circumference is 7.85 mm, and a maximum size for the aggregate circumference is 3.14 cm.

In another embodiment, the sleeve further defines a plurality of apertures through an inner surface of the sleeve to an outer surface of the sleeve. In some cases, at least one distal end of the plurality of optical fibers is positioned to pass through an aperture of the plurality of apertures. In some cases, the plurality of apertures are uniformly spaced with respect to each other. In some cases, each aperture is configured to control the angle of bend for an optical fiber passing through a corresponding aperture.

In another embodiment, the plurality of optical fibers include shape-memory optical fibers.

In another aspect, a method can include inserting the distal ends of the plurality of optical fibers of the endoscope into a biopsy channel; and repositioning the sleeve with respect to the distal ends of the plurality of optical fibers.

This aspect can include a variety of embodiments. In one embodiment, repositioning the sleeve includes moving the sleeve away from the distal ends of the plurality of optical fibers.

In another embodiment, the method further includes expanding an aggregate circumference defined by the distal ends of the plurality of optical fibers based on the repositioning of the sleeve.

In another embodiment, repositioning the sleeve causes at least one of the plurality of optical fibers to experience a bend radius along the length of the optical fiber of 10 mm.

In another embodiment, the method can further include capturing at least one image from the plurality of optical fibers subsequent to the repositioning of the sleeve. In some cases, a field of view (FOV) range for a captured image is 1 cm in diameter. In some cases, the at least one image includes a fluorescence image.

In another embodiment, the method can further include capturing photoacoustic signals, microstructured optical waveguides, or Raman scattering from the plurality of optical fibers subsequent to the repositioning of the sleeve.

In another embodiment, the method can further include receiving a plurality of images from a subset of the plurality of optical fibers; and calculating, via a machine-learning algorithm, a set of image parameters corresponding to the plurality of images. In some cases, the method can further include generating, via the machine-learning algorithm, an aggregated image from the plurality of images and the calculated set of image parameters.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIG. 2A depicts a side perspective of an end-expandable optical fiber bundle in a collapsed mode; FIG. 2B depicts a cross-sectional perspective of an end-expandable optical fiber bundle in a collapsed mode; FIG. 2C depicts a side perspective of an end-expandable optical fiber bundle in an expanded mode; and FIG. 2D depicts a cross-sectional perspective of an end-expandable optical fiber bundle in an expanded mode.

DEFINITIONS

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

End-Expandable Optical Fiber Bundle System

Figure 1:
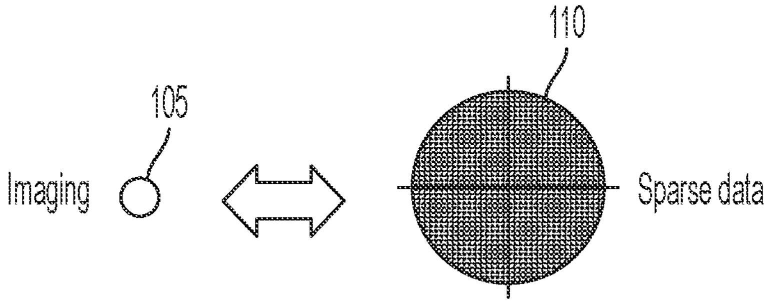
FIG. 1 illustrates data collection of collapsed and expanded fiber optic bundles, according to an embodiment of the claimed invention.

Systems of end-expandable optical fiber bundles are described herein. The optical fiber bundle can include a distal end having a variable cross-sectional area. The cross-sectional area of the optical fiber bundle can expand or contract according different mechanisms used to alter the cross-sectional area of the bundle. Once expanded, the fiber optic bundle can receive images, for example, of a sample that can be collected. The images received can have an increased field of view (FOV) compared to the fiber optic bundle when collapsed (e.g., with a smaller cross-sectional area), which can aid in high-yield screening, testing, and minimally invasive treatment of a patient. FIG. 1 illustrates FOVs for an optical fiber bundle in a collapsed mode (e.g., FOV 105) and an expanded mode (e.g., FOV 110). As shown, an optical fiber bundle with an expanded cross-sectional area can also include an increased FOV for image and data capturing, compared to the optical fiber bundle with a collapsed cross-sectional area. For example, in some cases the FOV range can be between about 0.1 mm to about 1 cm in diameter

Optical Fiber Bundle

The end-expandable optical fiber bundle can include a plurality of optical fibers. The optical fiber bundle can include a number of individual optical fibers, where the number can vary. For example, the optical fiber bundle can include between about 16 and 64 (e.g., 33, 36, and the like), 100 fibers, 1,000 fibers, 10,000 fibers, 100,000 fibers, 1,000,000 fibers, and the like. In practice, the number of individual optical fibers used in the system can be influenced based on collapsed cross-section size, weight of the system, processing ability of coupled processors, and the like.

The optical fibers can also include various characteristics. For example, the length of the optical fibers can vary based on the desired application from several millimeters to tens of centimeters (e.g., GI tract upper and lower endoscopy, anoscopy, arthroscopy, hysteroscopy, and the like). Further, the diameter of the optical fibers can vary. For example, the diameter of an optical fiber can be 5 μm, 100 μm, 300 μm, and the like. The optical fibers can be single mode fibers, multimode fibers, microstructured fibers, and the like. The number of optical fibers can vary as well, and can be dependent in some cases on the number of slots defined by the bundle sleeve. Other characteristics can vary as well, such as the finishing and/or polishing on the exterior surfaces of the optical fibers. In some cases, fiber connectors may be applied The bundle of optical fibers can be coupled at the proximal end. Coupling can occur through adhesive, wrapping or cordage around the aggregated circumference of the optical fiber bundle, through a sleeve over the aggregated circumference of the bundle, and the like. In some cases, the bundle can be separated into groups of optical fibers, where the distal ends of each group are coupled.

The distal ends of the optical fibers can remain uncoupled. In some cases, each optical fiber can be uncoupled to the other optical fibers in the bundle. In other cases, the optical fibers can be separated into groups (e.g., different or same as the groups discussed with respect to the proximal end couplings) of optical fibers, such that distal ends of optical fibers in the same group are coupled to one another.

Optical Fiber Sleeve

The optical fiber bundle can be enclosed in a sleeve or sheath. The sleeve can encompass the optical fiber bundle, and can span between the proximal ends and the distal ends of the bundle. Further, the inner cross-sectional area of the sleeve can be approximately the aggregated cross-sectional area of the optical fiber bundle when collapsed (e.g., unexpanded), thereby maintaining the unexpanded cross-sectional area of the bundle for whichever portions of the bundle are enclosed by the sleeve. The sleeve can be composed of polyvinyl chloride (PVC), polyethylene, polyurethane, polybutylene terephthalate, polyamide, nylon, polyolefin, monocoil, stainless interlock, silicone, polytetrafluoroethylene (PTFE) (e.g., TEFLON® available from The Chemours Company of Wilmington, Delaware), synthetic mesh, and the like. The sleeve can be biocompatible and compatible with medical or surgical lubricants that may be applied to ease advancement of the system. In some cases, the sleeve can also include a collet clamping mechanism, which can be configured to reduce the cross-sectional area of the lumen defined by the sleeve.

Expander

Figure 4:
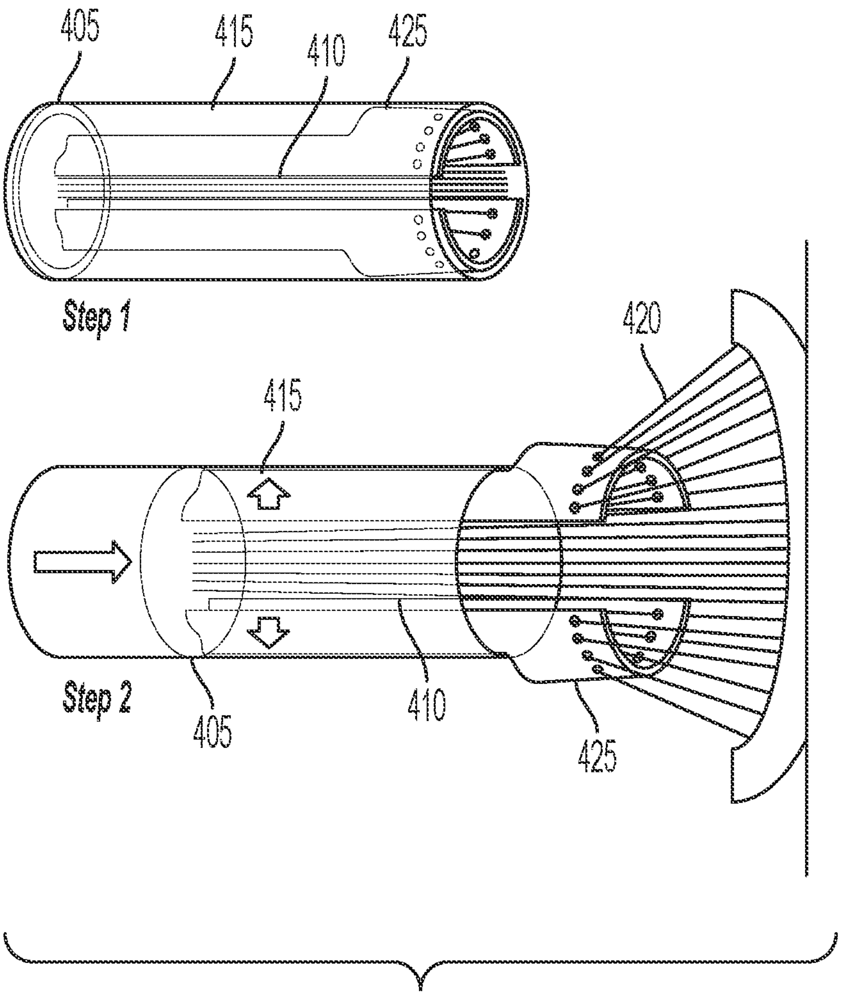
FIG. 4 depicts an expansion plunger and collar, according to an embodiment of the claimed invention.

The optical fiber bundle system can also include an expander. The expander can force the distal ends of the optical fiber bundle past the sleeve enclosure. In some cases, the expander can equalize the distal ends in the same plane. As the distal ends of the bundle are uncoupled, forcing the distal ends past the sleeve enclosing allows for the distal ends of the bundle to expand, which can subsequently create a larger aggregated cross-sectional area defined by the distal ends. In some cases, the expander can be a plunger or grip in contact with the proximal ends of the bundle. The plunger can push the proximal ends of the bundle towards the distal ends of the bundle. This force can cause the bundle to move in relation to the bundle sleeve enclosing the bundle, which can further result in the distal ends of the bundle exiting the sleeve. Further, the plunger can also pull the proximal ends away from the distal end, which can result in retracting the distal ends of the bundle into the sleeve. An example of a plunger is depicted in FIG. 4. Step 1 of FIG. 4 illustrates a collapsed mode of the optical fiber bundle 410, with a plunger 405 not applying force (e.g., enough force to displace the optical fiber bundle 410) to the proximal ends. As shown in Step 2, the plunger 405 applies force to the proximal ends of the optical fiber bundle sufficient to distally displace the bundle 410 in relation to a bundle sleeve 415, thereby expanding the cross-sectional area of the distal ends 420 of the bundle 410.

In some embodiments, advancement and retraction of the scope and the optical fibers within the same can be controlled by a machine. For example, the scope and the optical fibers can be each coupled to an actuator such as a servo.

Actuation of the actuator can be performed using feedback. For example, images from the distal end of the optical fibers and/or current or resistance from the actuator can be captured in real-time. These inputs can detect when the scope and/or the fibers are approaching and/or contacting an object (e.g., luminal wall) and slow, stop, or reverse advancement.

Likewise, the actuator can utilize feedback to implement a pre-defined scan to capture an area or interest. Such a scan may be iterative in which the scope advances a distance, the fibers are advanced relative to the sleeve, an image is capture, and the fibers are retracted before the cycle repeats. The images can be captured and saved to memory and further processing (e.g., using artificial intelligence, machine learning, and the like).

Expanded and Collapsed Bundle Circumference

Figure 2A:
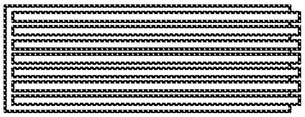
FIGS. 2A-2D depict different perspectives of an end-expandable optical fiber bundle, according to embodiments of the claimed invention.
Figure 2B:
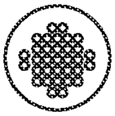
Figure 2C:
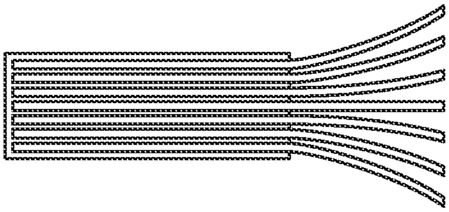
Figure 2D:
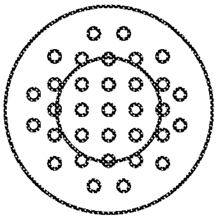

The size of the aggregated cross-sectional area (and therefore the circumference) defined by the distal end, when expanded (e.g., the distal ends are not enclosed by the sleeve), may be dependent on the distance the distal ends of the fibers are away from the distal end of the sleeve, and the curvation radius of each optical fiber. In some cases, the curvation radius of the optical fiber can be dependent on the composition of the optical fiber, as well as in cases if the distal ends of the fibers are coupled in groups as discussed above. In some cases, a minimum size (e.g., collapsed) for the aggregate circumference of the bundle distal ends is 7.85 mm. Further, in some cases a maximum size (e.g., fully expanded) for the aggregate circumference of the bundle distal ends is 3.14 cm. FIGS. 2A-2D depicts different perspectives of an optical fiber bundle in collapsed and expanded modes. FIGS. 2A and 2B depict perspectives of an optical fiber bundle in a collapsed mode, and FIGS. 2C and 2D depict perspective of an optical fiber bundle in an expanded mode.

Optical Fiber Guide Slots

In some cases, the optical fiber bundle system can also include a plurality of guide slots (apertures) located on the distal end of the bundle sleeve. The guide slots can pass through the interior surface of the sleeve to the exterior surface of the sleeve, and may be configured to receive an optical fiber distal end of the bundle. The guide slot can control the direction at which the received optical fiber exits the sleeve, which can thereby control the size of the expanded circumference of the bundle distal end. This directional control can be based on the size and location of the guide slot, as well as in some cases the angle of guide slot with respect to the interior and exterior surfaces of the sleeve. Exemplary angles relative to a central axis of the scope/expander include between about 5° and about 45°, between about 5° and about 15°, between about 15° and about 30°, between about 30° and about 45°, and the like. In some cases, the guide slots can take different shapes, such as for example, a helical shape defined by the sleeve, or the sleeve can define a distributing bracket for guiding an optical fiber.

In some cases, the guide slots can be located on an expander collar, which can be displaceable along the length of a corresponding bundle sleeve. The collar can in some cases also expand and collapse, for example the two-piece collar 425 shown in FIG. 4. The collar 425, during a collapsed mode for the bundle 410, can be collapsed itself and positioned within the interior of the sleeve 415. However, in the expanded mode, the collar 425 can be positioned distally exterior to the sleeve 410, at which point the collar 425 can expand to radially an expanded cross-sectional area.

Image Capturing

Figure 3:
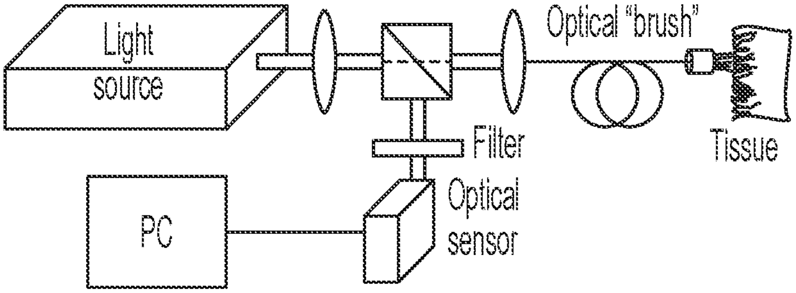
FIG. 3 depicts an image capturing system including an end-expandable optical fiber bundle according to an embodiment of the claimed invention.

In some cases, the optical fiber bundle system can be a part of an image and data capturing system, such as the system depicted in FIG. 3. The optical fiber bundle can be optically coupled to a camera (e.g., optical sensor such as a CCD, CMOS, and the like). The optical sensor can receive images from the optical fiber bundle, which can then be relayed to a processor for image processing. The system can identify approximate fiber distal end positions based on fiber type, length, bend radius, sectioning within the guide at the distal and proximal ends, and the like. Based on this approximate position, the system can also spatially divide and analyze the captured data from the optical fibers. When in expanded form, the optical fiber bundle can capture a images corresponding to a larger frame of view (FOV) compared to images captured in a collapsed form. Further, captured images can also correspond to sparse data imaging, which can facilitate high-yield screening and testing in certain endoscopic applications.

Applications

In some cases, the optical fiber system can implement fluorescein dyes for image capture. Fluorescein dyes, which have been tested as topical contrast agents and are demonstrated as high efficiency and safety, can be applied to differentiate neoplasia from non-neoplasia in stained tissue. The results can contain quantitative sensing data that can be compared to quantitative microscopic imaging data. Also, it has been demonstrated that fluorescein, which is an intravenous specific contrast agent, can also be used as an efficient and safe topical dye.

Fluorescence emitted from the sample can be measured with a silicon photodiode (e.g., an optical sensor). A low-noise transimpedance amplifier can be used to convert optical response into a voltage. An optical bandpass filter can be used to collect only fluorescence emission. A photodiode can be used at output of the light source to monitor emission fluctuations and normalize the detected signal.

A region of tissue without applied dye can provide the measure of incident light to estimate relative light excitation in tissue samples. Optical density of the filtered light can be measured fiber-by-fiber. Then, histograms can be plotted for normal tissue and different levels of dysplasia and neoplasia. The histogram areas can be used to identify thresholds and differentiate normal, pre-cancerous, and cancerous tissue. Integral optical density can be computed for whole FOV or each of four quadrants of FOV.

In cases of sparse, low resolution imaging, the images can be enhanced via deep learning super-resolution algorithms that preserve diagnostic accuracy as compared to microendoscopy images acquired at high resolution. Further, machine learning models can be trained to classify sparse images and/or sensing data by itself. For example, machine learning models can perform direct calculations of image parameters relevant to clinical features of endoscopic images. In another example, machine learning models can reconstruct sparse images into images suitable for further analysis.

In another example, application of the optical fiber system can be expanded to molecule-specific biomarker-targeted imaging using optical contrast agents. Other applications may include photoacoustic monitoring; microstructured optical waveguide sensing, Raman scattering detection. In some cases, the optical fiber system can be used for accurate sensing with tunable hollow-core optical fibers for precise sampling and targeted drug delivery as minimally-invasive treatment.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. An endoscope comprising:

a plurality of optical fibers each having a proximal end and a distal end;

at least one camera coupled to the proximal ends of the plurality of optical fibers; and a sleeve enveloping the plurality of optical fibers proximate to the distal ends and repositionable along the length of the plurality of optical fibers, such that the sleeve is configured to control an angle of bend for each of the plurality of optical fibers as the optical fibers advance past the sleeve, wherein the distal ends of the plurality of fiber optics define an aggregate circumference perpendicular to the length of the plurality of fiber optics, wherein the aggregate circumference is variable based on the position of the sleeve with respect to the distal ends and the angle of bend for each of the plurality of optical fibers.

2. The endoscope of claim 1, wherein the plurality of optical fibers are uncoupled to one another.

3. The endoscope of claim 1, wherein a minimum size for the aggregate circumference is 7.85 mm, and a maximum size for the aggregate circumference is 3.14 cm.

4. The endoscope of claim 1, wherein the sleeve further defines a plurality of apertures through an inner surface of a wall of the sleeve to an outer surface of the wall of the sleeve.

5. The endoscope of claim 4, wherein at least one distal end of the plurality of optical fibers is positioned to pass through an aperture of the plurality of apertures.

6. The endoscope of claim 4, wherein the plurality of apertures are uniformly spaced with respect to each other.

7. The endoscope of claim 4, wherein each aperture is configured to control the angle of bend for an optical fiber passing through a corresponding aperture.

8. The endoscope of claim 1, wherein the plurality of optical fibers comprise shape memory optical fibers.

9. A method comprising:

inserting the distal ends of the plurality of optical fibers of the endoscope of claim 1 into a biopsy channel; and repositioning the sleeve with respect to the distal ends of the plurality of optical fibers.

10. The method of claim 9, wherein repositioning the sleeve comprises moving the sleeve away from the distal ends of the plurality of optical fibers.

11. The method of claim 9, further comprising expanding an aggregate circumference defined by the distal ends of the plurality of optical fibers based on the repositioning of the sleeve.

12. The method of claim 9, wherein repositioning the sleeve causes at least one of the plurality of optical fibers to experience a bend radius along the length of the optical fiber of 10 mm.

13. The method of claim 9, further comprising capturing at least one image from the plurality of optical fibers subsequent to the repositioning of the sleeve.

14. The method of claim 13, wherein a field of view (FOV) range for a captured image is 1 cm in diameter.

15. The method of claim 13, wherein the at least one image comprises a fluorescence image.

16. The method of claim 9, further comprising capturing photoacoustic signals, microstructured optical waveguides, or Raman scattering from the plurality of optical fibers subsequent to the repositioning of the sleeve.

17. The method of claim 9, further comprising:

receiving a plurality of images from a subset of the plurality of optical fibers; and calculating, via a machine-learning algorithm, a set of image parameters corresponding to the plurality of images.

18. The method of claim 17, further comprising:

generating, via the machine-learning algorithm, an aggregated image from the plurality of images and the calculated set of image parameters.

* * * * *